United States Patent
Serban et al.

(10) Patent No.: US 8,826,724 B2
(45) Date of Patent: Sep. 9, 2014

(54) CARBON DIOXIDE SENSOR

(75) Inventors: Bogdan Serban, Bucharest (RO); Mihai N. Mihalia, Bucharest (RO); Cornel Cobianu, Bucharest (RO); Viorel Georgel Dumitru, Ploiesti (RO); Octavian Buiu, Bucharest (RO)

(73) Assignee: Honeywell International Inc., Morristown, NJ (US)

( * ) Notice: Subject to any disclaimer, the term of this patent is extended or adjusted under 35 U.S.C. 154(b) by 203 days.

(21) Appl. No.: 13/333,752

(22) Filed: Dec. 21, 2011

(65) Prior Publication Data

US 2012/0164029 A1    Jun. 28, 2012

(30) Foreign Application Priority Data

Dec. 24, 2010  (EP) .................................... 10196990

(51) Int. Cl.
| | | |
|---|---|---|
| *G01N 29/00* | (2006.01) | |
| *G01N 29/036* | (2006.01) | |
| *G01N 29/22* | (2006.01) | |
| *G01N 29/02* | (2006.01) | |
| *G01N 33/00* | (2006.01) | |

(52) U.S. Cl.
CPC ...... *G01N 29/022* (2013.01); *G01N 2291/0427* (2013.01); *G01N 29/036* (2013.01); *G01N 2291/0257* (2013.01); *G01N 2291/0255* (2013.01); *G01N 33/004* (2013.01)
USPC ............. 73/24.01; 73/24.08; 422/82; 422/83; 422/98

(58) Field of Classification Search
USPC ............ 73/23.2, 24.01–24.06; 422/50, 83, 98
See application file for complete search history.

(56) References Cited

U.S. PATENT DOCUMENTS

| | | |
|---|---|---|
| 3,904,486 A | 9/1975 | Faurschou et al. |
| 3,926,724 A | 12/1975 | Takayama et al. |
| 4,025,412 A | 5/1977 | LaConti |

(Continued)

FOREIGN PATENT DOCUMENTS

| | | |
|---|---|---|
| CA | 2283563 A1 | 11/1998 |
| DE | 3939166 A1 | 5/1991 |

(Continued)

OTHER PUBLICATIONS

Galipeau et al., The integration of a chemiresistive film overlay with a surface acoustic wave microsensor, Sensors and Actuators B 35-36 (1996) 158-163.*

(Continued)

*Primary Examiner* — Paul Hyun
*Assistant Examiner* — Robert Eom
(74) *Attorney, Agent, or Firm* — Seager Tufte & Wickhem LLC

(57) ABSTRACT

Chemical sensors such as carbon dioxide sensors and methods for making such sensors are disclosed. An example carbon dioxide sensor may include a substrate, with a sensing beam supported by the substrate. The sensing beam may be configured to resonant. A sensing layer may be disposed on the sensing beam, wherein the sensing layer may include an amino group and is configured to sense carbon dioxide. In some instances, a reference beam may also be supported by the substrate, and may be configured to resonant. A reference layer may be disposed on the reference beam, wherein the reference layer may includes an amino group that has been poisoned so that it will be substantially non-sensitive to carbon dioxide.

10 Claims, 6 Drawing Sheets

(56) References Cited

U.S. PATENT DOCUMENTS

| | | | |
|---|---|---|---|
| 4,123,700 | A | 10/1978 | LaConti et al. |
| 4,171,253 | A | 10/1979 | Nolan et al. |
| 4,269,682 | A | 5/1981 | Yano et al. |
| 4,708,905 | A | 11/1987 | Yoshii et al. |
| 4,851,088 | A | 7/1989 | Chandrasekhar et al. |
| 5,160,597 | A | 11/1992 | Colapicchioni et al. |
| 5,271,820 | A | 12/1993 | Kinlen et al. |
| 5,322,612 | A | 6/1994 | Abe et al. |
| 5,625,139 | A | 4/1997 | Stormbom |
| 5,668,302 | A | 9/1997 | Finbow et al. |
| 5,756,879 | A * | 5/1998 | Yamagishi et al. .......... 73/28.01 |
| 6,094,335 | A | 7/2000 | Early |
| 6,358,384 | B1 | 3/2002 | Warburton |
| 6,426,861 | B1 | 7/2002 | Munshi |
| 6,456,943 | B1 | 9/2002 | Kogure et al. |
| 6,483,694 | B1 | 11/2002 | Monden et al. |
| 6,632,674 | B1 | 10/2003 | Warburton |
| 6,948,352 | B2 | 9/2005 | Rabbett et al. |
| 7,174,766 | B2 | 2/2007 | Eickhoff et al. |
| 7,318,887 | B2 | 1/2008 | Rhodes |
| 7,468,608 | B2 | 12/2008 | Feucht et al. |
| 7,628,907 | B2 | 12/2009 | Gu et al. |
| 7,628,957 | B1 | 12/2009 | Moseley et al. |
| 7,691,583 | B2 | 4/2010 | Craighead et al. |
| 7,713,336 | B2 | 5/2010 | Hengsperger |
| 7,774,930 | B2 | 8/2010 | Tai et al. |
| 2002/0065332 | A1 | 5/2002 | Choi et al. |
| 2002/0157447 | A1 | 10/2002 | Schell |
| 2003/0145644 | A1 | 8/2003 | Rabbett et al. |
| 2004/0018632 | A1 | 1/2004 | Shabana et al. |
| 2004/0050142 | A1 | 3/2004 | Hok |
| 2004/0158410 | A1 | 8/2004 | Ono et al. |
| 2004/0206906 | A1 | 10/2004 | Owen |
| 2005/0077179 | A1 | 4/2005 | Rhodes |
| 2005/0262924 | A1 | 12/2005 | Wood et al. |
| 2006/0266096 | A1 | 11/2006 | Eickhoff et al. |
| 2008/0196478 | A1 | 8/2008 | Raghurama et al. |
| 2008/0216558 | A1 | 9/2008 | Koyilothu et al. |
| 2008/0264147 | A1 | 10/2008 | Serban et al. |
| 2009/0233058 | A1 | 9/2009 | Hata et al. |
| 2010/0060393 | A1 | 3/2010 | Joo et al. |

FOREIGN PATENT DOCUMENTS

| | | | |
|---|---|---|---|
| DE | 10220668 A1 | | 11/2003 |
| EP | 0355896 | | 2/1990 |
| EP | 0708328 | | 4/1996 |
| EP | 0890837 | | 1/1999 |
| GB | 1217625 | | 12/1970 |
| GB | 1398977 | A | 6/1975 |
| GB | 2356708 | A | 5/2001 |
| GB | 2457153 | A | 8/2009 |
| JP | 03123848 | A | 5/1991 |
| JP | 08220063 | A | 8/1996 |
| JP | 08220064 | | 8/1996 |
| JP | 11014586 | A | 1/1999 |
| WO | 9635116 | A1 | 11/1996 |
| WO | 9917110 | A1 | 4/1999 |
| WO | 03056325 | | 7/2003 |
| WO | 2005026694 | A2 | 3/2005 |
| WO | 2005026694 | A3 | 8/2006 |
| WO | 2007008483 | | 1/2007 |
| WO | 2008103631 | A1 | 8/2008 |
| WO | 2010239307 | | 4/2010 |

OTHER PUBLICATIONS

Avramescu et al., Surface acoustic wave devices and their sensing capabilities, Semiconductor Conference, 2009. CAS 2009. International (Colume: 1), 27-36.*

Huang et al., Why are ionic liquids attractive for $CO_2$ absorption?, Aust. J. Chem. 2009, 62, 298-308.*

Matsuo, et al., "Characteristics of Reference Electrodes Using a Polymer Gate ISEFET," Sensor and Actuators, 5, 1984, pp. 293-305.

Diefenderfer, "Principles of Electronic Instrumenation," $2^{nd}$ Edition, p. 159, 226, 1979. ISBN 0-7216-3076-6.

Nakajima et al., "The Cation Concentration Response of Polymer Gate ISFET," Department of Electronic Engineering, Tohoku University, Sendai Japan, p. 141-143. Jan. 1982.

R. Zhou, et al., "Reliable CO2 sensors with silicon-based polymers on quartz microbalance transductors," University of Tubingen Germany, pp. 415-420, 1994. Sensors and Actuators B, 18-19.

Illchat Goubaidoulline et al., "Organic Vapor Sensing with Ionic Liquids Entrapped in Alumina Nanopores on Quartz Crystal Resonators," Institute of Physical Chemistry Germany, pp. 615-619, 2005.

M. Rocchia, "Sensing CO2 in a chemically modified porous silicon film," Department of Materials Secience and Chemical Engineering Turin Italy, pp. 365-369, 2003.

Pinkerton et al., "Bottling the Hydrogen Genie," The Industrial Physicist, vol. 10, No. 1, p. 20-23, Feb./Mar. 2004.

Bettelheim, et al., "A New Polymer AglAgCl Reference Electrode for Electrochemisty with No Contacting Electrolyte Solution," Journal of the Electrochemical Society, 44, 1988, pp. 1041-1042.

Bin Yu et al., "Controllable Zeolite Films on Electrodes—Comparing DC Voltage Electrophoretic Deposition and a Novel Pulsed Voltage Method," Electrochemistry Communication, vol. 4, No. 10, Oct. 2002, pp. 737-742.

Christiasen, "The Achilles' Heal of Potentiometric Measurements, the Liquid Junction Potential," IEEE Transactions of Biomedical Engineering, 33,2,1986, pp. 79-82.

Covington, A.K., et al., "Reference Electrodes and Liquid Junction Effects in Ion-Selective Electrode Potentiometry," Ion Selective Review, 5, 1983, pp. 93-128.

Desmond, et al., "Evaluation of Miniaturized solid State Reference Electrode on a Silicon-Based Substrate," Sensor and Actuators B, 44, 1997, pp. 389-396.

Eine, et al., "Towards a Solid-State Reference Electrode," Sensors and Actuators B, 44,1997, pp. 381-388.

Huang, et al., "A New Structures ISFET with Integrated Ti/Pd/Ag/AgCl Electrode and Micromachined Back-Side P+ Contacts," Journal of Chinese Institute of Engineers, 2002, 25(3), pp. 327-334.

Huang et al., "Fabrication and Characterization of a New Planar Solid-State Reference Electrode for ISFET Sensors," Thin Solid Films, 2002, 406(1-2) pp. 255-261.

Hyuk Jin Lee, et al, "Solvent-Processible Polymer Membrane-Based Liquid Junction-Free Reference Electrode," Anal. Chem., 701161, pp. 3377-3383, Aug. 15, 1988.

Kwang-Seok, et al, "Analysis of Heavy-Metal Ions Using Mercury Microelectrodes and a Solid-State Reference Electrode of a Si Wafer," in Japan Soc. Appl. Phys. Japanese Journal of Applied Physics Part 1—Regular Papers Short Notes & Review Papers, vol. 39, No. 12B, Dec. 2000 pp. 7159-7163.

Levitchev, et ],, "Photocurable Carbonate-Selective Membranes for chemical Sensors Containing Lipophilic Additives," Sensors and Actuators B., 44. 1997, pp. 397-401.

Margules, et al., "Functional Mechanisms of Polymer-Based in Vivo Reference electrodes" J Biomed, Eng. 9, 1987, pp. 21-25.

Matysik et al., "A Disposable Electrode Based on Zeolite-Polymer Membranes for Potentiometric Titrations of Ionic Surfactants," Sensors and Actuators B-Chemical, vol. B85 No. 1-2 Jun. 20, 2002, pp. 104-108.

Smith, R.L., et al, "An integrated Sensor for Electrochemical Measurements," IEEE Transactions on Biomedical Engineering, 33, 2, 1986, pp. 307-310.

Nagy, et al., "Promising New Solid-State Reference Electrode," Electrochemical Society Letters, 144, Til, 1977,L1-L2.

Sandifer, "Theory of Interfacial Potential Differences: Effects of Adsorption onto Hydrated (Gel) and Nonhydrated Surfaces," Analytical Chemistry, 60, 1988. pp. 1553-1564.

Tahara, et al., "Electrochemical Reference Electrode for the Ion-Selective Field Effect Transistor," Chemistry Letters (The Chemistry Society of Japan), 1982, pp. 307-310.

(56) References Cited

OTHER PUBLICATIONS

Yousefi, "Studies on Mixed Transition Metal Dichalcogenide-Electrolyte Interfaces," Crystal Research and Techonlgy, 25, 6, 1990, pp. 125-129.

Yun, San Yong, et al., "Potentiometric Properties of Ion-Selective Electrode Membranes Based on Segmented Polyether Urethane Matrices," Journal of the American Chemical Society, 69, [5], 1977, pp. 868-873.

* cited by examiner

CARBON DIOXIDE SENSOR

This application is based upon and claims the benefit of priority from European Patent Application No. 10196990, filed on Dec. 24, 2010, the entire content of which is incorporated herein by reference.

TECHNICAL FIELD

The present disclosure relates to chemical sensors, and more particularly, to carbon dioxide sensors that include a sensing layer with an amino group.

BACKGROUND

A wide variety of sensors have been developed for sensing small molecules such as, for example, carbon dioxide. These sensors operate under a variety of different principles and are manufactured using a variety of different manufacturing methods. Of the known sensors and methods, each has certain advantages and disadvantages. There is an ongoing need for alternative chemical sensors as well as alternative methods for manufacturing and using such chemical sensors.

SUMMARY

This disclosure provides design, material, manufacturing methods, and use alternatives for chemical sensors such as carbon dioxide sensors. An example chemical sensor may include a carbon dioxide sensor that has a silicon chip or other substrate. A sensing beam may be supported by (e.g. disposed on or formed in or by) the chip. In some cases, the sensing beam may be a resonant beam that resonates or vibrates during a sensing operation. In some instances, the sensing beam may be a cantilevered beam that cantilevers out over part of the chip. In other cases, the sensing beam may be a bridge. In yet other instances, the sensing beam may be considered the resonating part of a Surface Acoustical Wave (SAW) sensor. These are just some examples. Regardless of the form of the sensing beam, a sensing layer may be disposed on the sensing beam. The sensing layer may include an amino group that is suitable for absorbing a chemical of interest, such as carbon dioxide. In some instances, a reference beam may be supported by (e.g. disposed on or formed in or by) the chip, with a reference layer disposed on the reference beam. In some instances, the reference layer may be the same or substantially the same as the sensing layer, but may be poisoned such that it does not substantially absorb the chemical of interest (e.g. carbon dioxide). Poisoning the reference layer may include applying an acid to the reference layer. Applying an acid to the reference layer may include a direct printing process.

The above summary is not intended to describe each and every embodiment or implementation. The Figures and Description which follow more particularly exemplify these certain illustrative embodiments.

BRIEF DESCRIPTION OF THE DRAWINGS

This disclosure may be more completely understood in consideration of the following description of various illustrative embodiments in connection with the accompanying drawings, in which.

Figure 1:
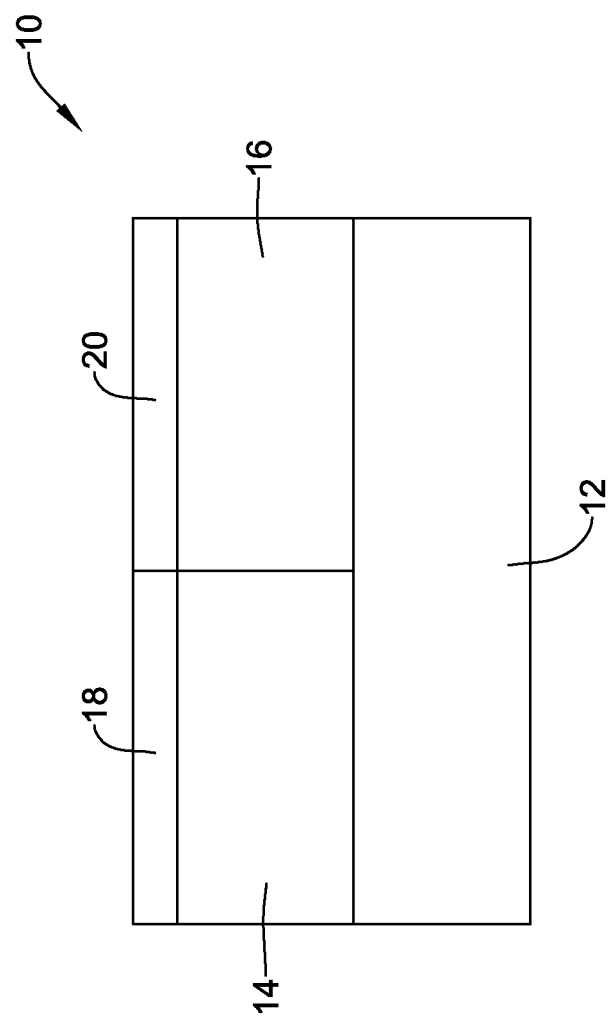
FIG. 1 is a schematic view of an illustrative sensor.

While the embodiments is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the invention.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used herein, the term "alkyl" refers to a straight or branched chain monovalent hydrocarbon radical having a specified number of carbon atoms. Alkyl groups include those with one to twenty carbon atoms or more. Alkyl groups may be unsubstituted or substituted with those substituents that do not interfere with the specified function of the composition. Substituents include alkoxy, hydroxy, mercapto, amino, alkyl substituted amino, or halo, for example. Examples of "alkyl" as used herein include, but are not limited to, methyl, ethyl, n-propyl, n-butyl, n-pentyl, isobutyl, and isopropyl, and the like.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings in which similar elements in different drawings are numbered the same. The drawings, which are not necessarily to scale, depict illustrative embodiments and are not intended to limit the scope of the invention.

Carbon dioxide is a stable molecule with a relatively low reactivity. Therefore, it can be challenging to manufacture carbon dioxide sensors for detecting the presence of carbon dioxide. The present disclosure pertains to sensors that may be sensitive to and, thus, can reliably sense carbon dioxide. In general, the sensors disclosed herein may include a sensing layer that includes a hard base under Pearson's hard soft acid base (HSAB) principle, such as an amino group. Because carbon dioxide is a hard acid, the resultant sensing layers may effectively and efficiently sense carbon dioxide molecules.

FIG. 1 illustrates and example chemical sensor 10. In some embodiments, sensor 10 may be carbon dioxide sensor. In at least some of these embodiments, sensor 10 may be a resonant carbon dioxide sensor. For example, sensor 10 may be silicon based resonant carbon dioxide sensor. Other sensors, however, are within the scope of the present disclosure. Sensor 10 may include a base, substrate or chip 12. Chip 12 may by any suitable substrate. For example, chip 12 may be a silicon wafer or silicon die. Other materials may also be used including, for example, glass, polymers, ceramics, metals, GaAs, or any other suitable material, as desired. Chip 12 may include one or more beams. For example, chip 12 may include or otherwise support a sensing beam 14, and in some instances, an adjacent reference beam 16 (e.g., both beams 14/16 may be disposed on or formed in or by the same chip 12).

In some cases, the sensing beam 14 may be a resonant beam that resonates or vibrates during a sensing operation. In some instances, the sensing beam 14 may be a cantilevered beam that cantilevers out over part of the chip 12. For example, in FIG. 1, the chip 12 may have a terminating face that lies in the plane of the page, and the sensing beam 14 may extend out of the page (similar to that shown in FIG. 2). In other cases, the sensing beam 14 may be a bridge over at least part of the chip 12. When present, the adjacent reference beam 16 may be formed in a similar manner. Such a sensing beam 14 and/or reference beam 16 can be readily manufactured using conventional MEMS manufacturing techniques, if desired. In some instances, the sensing beam 14 and/or reference beam 16 may be implemented as resonating part of a Surface Acoustical Wave (SAW) sensor, but this is not required. These are just some examples of a suitable sensing beam 14 and/or reference beam 16.

To complete the chemical sensor, a sensing layer 18 may be disposed on (e.g., on a surface of) the sensing beam 14. Likewise, a reference layer 20 may be disposed on (e.g., on a surface of) the reference beam 16, when provided. In some instances, the reference layer 20 may be the same or substantially the same as the sensing layer 18, but may be poisoned such that it does not substantially absorb the chemical of interest (e.g. carbon dioxide). Poisoning the reference layer 20 may include applying an acid to the reference layer 20, in some cases using a direct printing process.

During use, the sensing beam 14 and/or reference beam 16 may be vibrated at a resonance frequency. Over time, the sensing layer 18 may absorb the chemical of interest, which may change the mass of the sensing layer 18. This may change the resonance frequency of the sensing beam 14. This change in resonance frequency of the sensing beam 14 may be detected by control circuitry (not shown). The change in resonance frequency may be related to the concentration of the chemical of interest (e.g. carbon dioxide). To help compensate for changes in conditions (e.g. humidity, temperature, age, etc.), the reference beam 16 may provide a reference resonance frequency. The reference resonance frequency may change over time due to the changing conditions, and these changes may be independent from the concentration of the chemical of interest because the reference layer 20 on the reference beam 16 has been poisoned. The control circuitry (not shown) may use the output of the reference beam 16 to compensate the output of the sensing beam 14 for changes in conditions (e.g. humidity, temperature, age, etc.), thereby providing a more accurate result.

The composition of the sensing layer 18 may depend on the particular chemical of interest. For example, in sensors that are configured to sense carbon dioxide, sensing layer 18 may be designed and/or configured to sense carbon dioxide. Carbon dioxide may be considered a hard acid under Pearson's hard soft acid base (HSAB) principle. Accordingly, it is contemplated that sensing layer 18 may include one or more hard bases in order to efficiently sense carbon dioxide (e.g., more efficiently than soft bases or borderline bases). In some instances, sensing layer 18 may include one or more amino groups as a hard base. It is contemplated that other hard bases may also be used, if desired.

In some embodiments, sensing layer 18 may include a sensing ionic liquid that is, for example, disposed on sensing beam 14. The sensing ionic liquid may, in general, include an amino group. For example, the sensing ionic liquid may include an amino functionalized ionic liquid, 1-(4-amino butyl)-3 methylimidazolium hexafluorophosphate, 1-(2-amino ethyl)-3 methylimidazolium tetrafluoroborate, combinations thereof, or the like.

In other embodiments, sensing layer 18 may include a polymer or polymer layer that is, for example, disposed on sensing beam 14. The polymer layer may, in general, include an amino group or otherwise be an amino based polymer layer. For example, the polymer layer may include an amino group based polymer, N-substituted polyallylamine, polydiallylamine, polytriallylamine, polyvinlylamine, poly(y-aminoproplyethoxy/propylethoxysilones) (PAPP), poly(y-aminopropylethody octadecylethoxysiloxane) (PAPO), combinations thereof, or the like.

In still other embodiments, sensing layer 18 may include one or more nanotubes (e.g., a nanotube array) that is, for example, disposed on sensing beam 14. The nanotubes, in general, may include an amino group. For example, the nanotubes may be carbon nanotubes and/or may include amino functionalized carbon nanotubes, carbon nanotubes with aliphatic amino groups situated at the end of an alkyl chain (which may contain 1 to 20 or more carbon atoms), combinations thereof, or the like. In addition, it is contemplated that the nanotubes may be single-walled nanotubes, double-walled nanotubes, multi-walled nanotubes, nanowires (e.g., non-tubular wires or pillars), combinations thereof, or the like.

In some instances, sensing layer 18 may include the same sensing material (e.g., ionic liquid, polymer or polymer layer, nanotubes, etc.) along the entire surface of the layer 18. In other embodiments, however, sensing layer 18 may include multiple materials, sometimes formed as a composite layer. For example, sensing layer 18 may include an amino functionalized ionic liquid and an amino functionalized carbon nanotube composite, an amino functionalized ion liquid and an amino group based polymer or polymer layer composite, an amino functionalized carbon nanotube and an amino group based polymer or polymer layer composite, or the like. These are just some examples.

Figure 2:
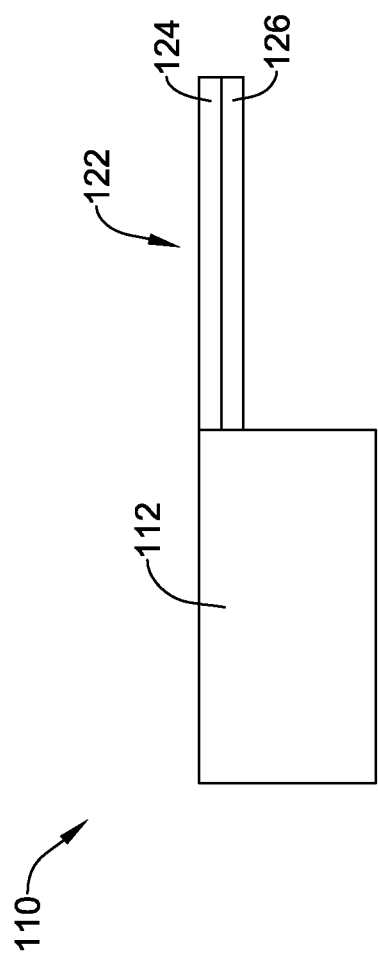
FIG. 2 is a schematic view of another illustrative sensor.

While FIG. 1 is a schematic illustration of sensor 10, the actual form of sensor 10 may vary considerably. For example, FIG. 2 illustrates an example sensor 110, which may be similar in form and function to sensor 10 of FIG. 1. Sensor 110 may include a base or chip 112 and a cantilever 122. Cantilever 122 may include a sensing layer 124. In some embodiments, sensing layer 124 may be disposed on a beam 126. However, this is not required.

Sensing layer 124 may be similar in form and function to sensing layer 18 and, thus, may include any of the materials described above in relation to sensing layer 18. For example, sensing layer 124 may include a sensing ionic liquid (e.g., that may include an amino group), a polymer or polymer layer (e.g., that may include an amino group or otherwise be an amino based polymer layer), one or more nanotubes (e.g., that may include an amino group), or be a composite including any suitable combination thereof. Also, it is contemplated that a cantilevered reference beam (not explicitly shown) may be positioned adjacent to cantilever 122 (such as in front or behind the cantilever 122 of FIG. 2). The reference beam may include a reference layer, and in some instances, the reference layer may be the same or substantially the same as the sensing layer 124, but may be poisoned such that it does not substantially absorb the chemical of interest (e.g. carbon dioxide).

Figure 3:
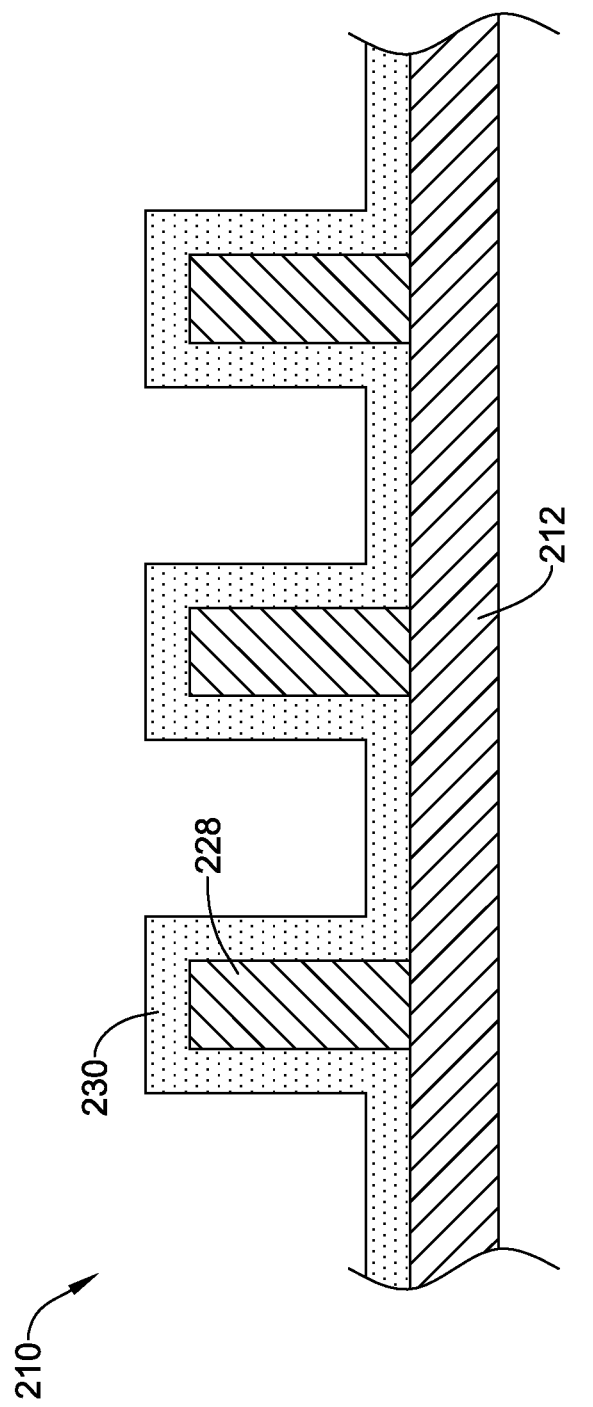
FIG. 3 is a partial cross-sectional side view of a portion of another illustrative sensor.

FIGS. 3-6 illustrate portions of illustrative sensors that include some of the nanotube/nanowire configurations contemplated that may be used with the sensing layers (e.g., sensing layers 18/124) and/or reference layers (e.g. reference layer 20) described herein. FIG. 3 illustrates a portion of a sensor 210 that includes a plurality of nanowires 228 disposed along a beam 212 (sensing or reference beam). Nanowires 228 may be amino functionalized in order to more efficiently sense, for example, carbon dioxide. This feature is illustrated in FIG. 3 as a sensing layer 230 that generally traces the surfaces of nanowires 228. Sensing layer 230 may be the same in form and function as sensing layers 18/124. The precise arrangement of nanowires 228 and/or sensing layer 230 may vary. For example, sensing layer 230 may be continuous, intermittent or broken, or otherwise include one or more localized amino functional groups disposed along nanowires 228. The nanowires 228 may increase the surface area of the sensing layer 230 relative to if the sensing layer 230 were provided on a planar surface. This may increase the sensitivity of the chemical sensor.

Figure 4:
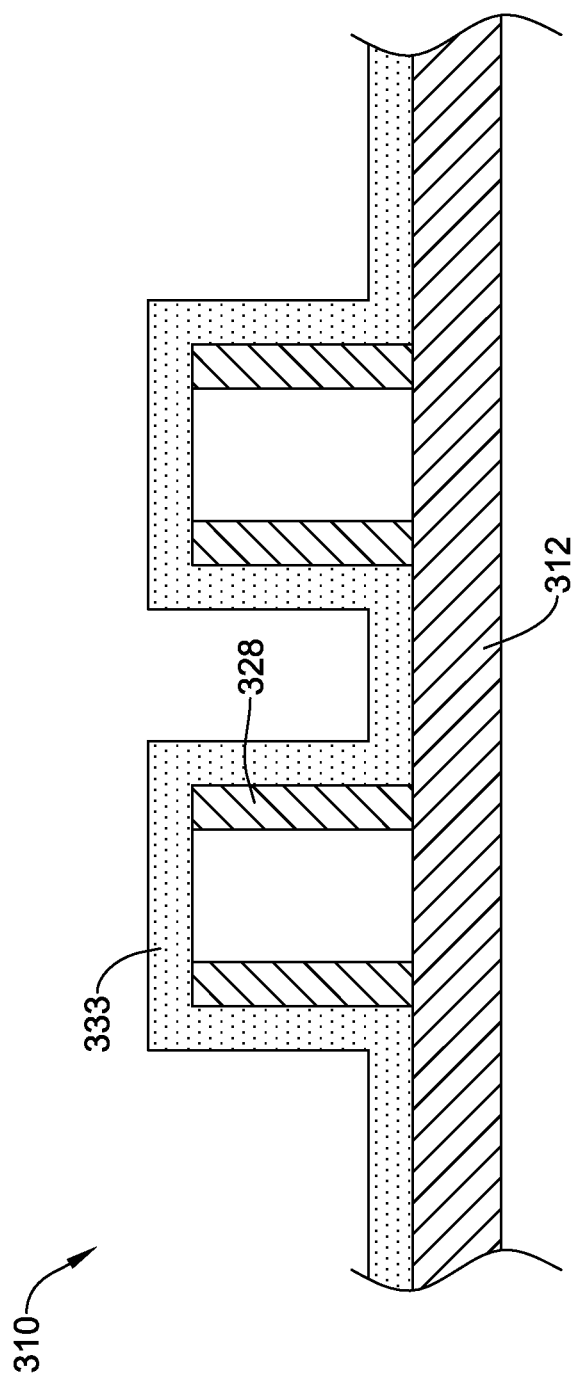
FIG. 4 is a partial cross-sectional side view of a portion of another illustrative sensor.

FIG. 4 illustrates a portion of sensor 310 including a plurality of nanotubes 328 disposed along a beam 312. In this embodiment, nanotubes 328 can be described as being "single-walled" nanotubes 328. Nanotubes 328 may be amino functionalized in order to more efficiently sense, for example, carbon dioxide. This feature is illustrated in FIG. 4 as a sensing layer 333 that generally traces the surfaces of nanotubes 328. In any event, sensing layer 333 may be the same in form and function as sensing layers 18/124/230 described above. The precise arrangement of nanotubes 328 and/or sensing layer 333 may vary. For example, sensing layer 333 may be continuous, may pass over the top of the nanotubes 328 as shown, may coat or even "fill in" the interior of nanotubes 328, be intermittent or broken, or otherwise include one or more localized amino functional groups disposed along nanotubes 328. The nanotubes 328 may increase the surface area of the sensing layer 333 relative to if the sensing layer 333 were provided on a planar surface. This may increase the sensitivity of the chemical sensor.

Figure 5:
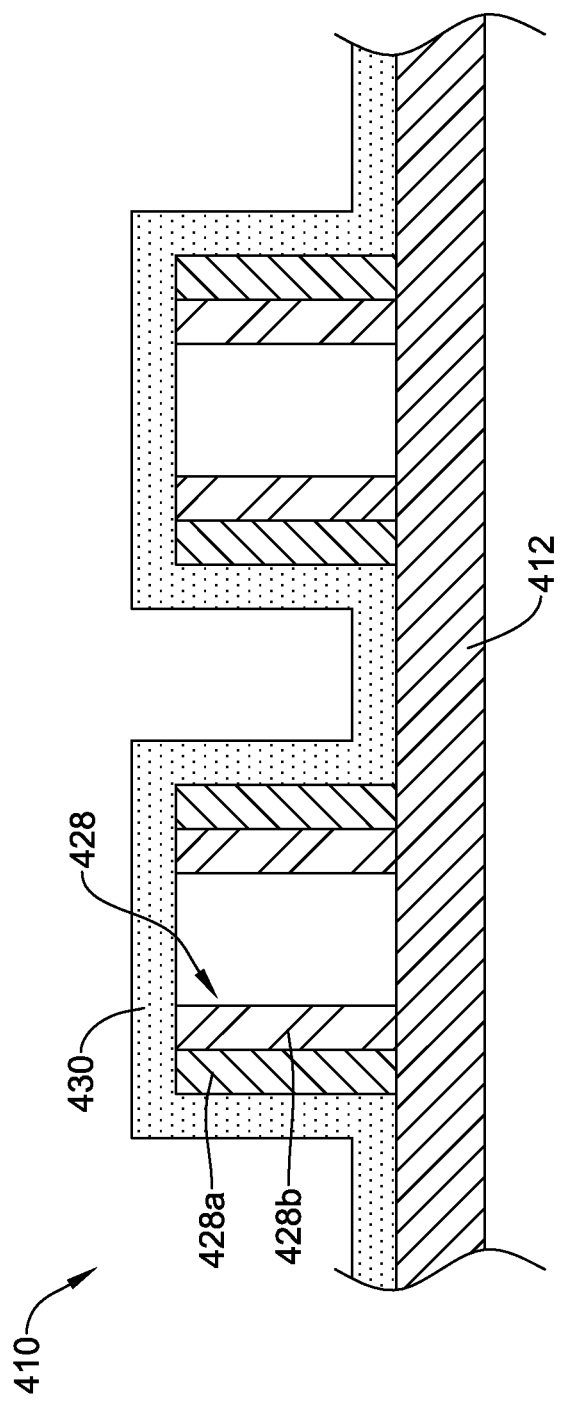
FIG. 5 is a partial cross-sectional side view of a portion of another illustrative sensor.

FIG. 5 illustrates a portion of sensor 410 including a plurality of nanotubes 428 disposed along a beam 412. In this embodiment, nanotubes 428 may be described as "double-walled" nanotubes 428 including a first wall layer 428a and a second wall layer 428b. Nanotubes 428 may be amino functionalized in order to more efficiently sense, for example, carbon dioxide. This feature is illustrated in FIG. 5 as a sensing layer 430 that generally traces the surfaces of nanotubes 428. Sensing layer 430 may be the same in form and function as sensing layers 18/124/230/333 described above. The precise arrangement of nanotubes 428 and/or sensing layer 430 may vary. For example, sensing layer 430 may be continuous, may pass over the top of the nanotubes 428 as shown, may coat or even "fill in" the interior of nanotubes 428, be intermittent or broken, or otherwise include one or more localized amino functional groups disposed along nanotubes 428.

Figure 6:
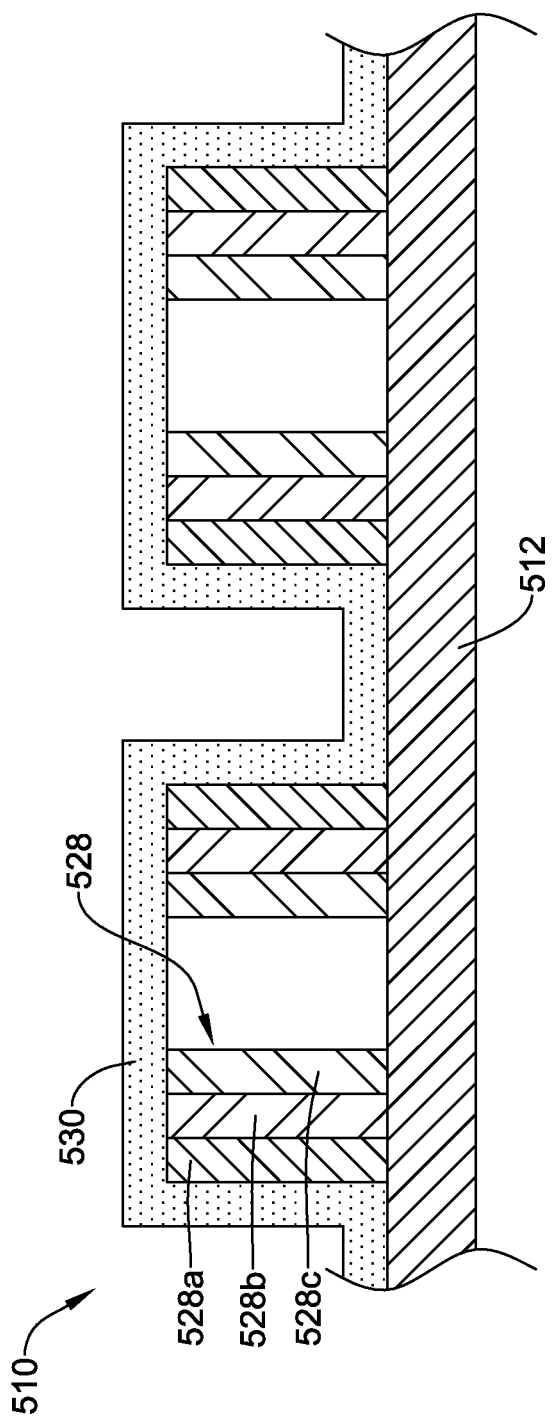
FIG. 6 is a partial cross-sectional side view of a portion of another illustrative sensor.

FIG. 6 illustrates a portion of sensor 510a plurality of nanotubes 528 disposed along a beam 512. In this embodiment, nanotubes 528 may be described as "multi-walled" nanotubes 528 including a first wall layer 528a, a second wall layer 528b, and a third wall layer 528c. Other embodiments are contemplated that include additional wall layers. Nanotubes 528 may be amino functionalized in order to more efficiently sense, for example, carbon dioxide. This feature is illustrated in FIG. 6 as a sensing layer 530 that generally traces the surfaces of nanotubes 528. Sensing layer 530 may be the same in form and function as sensing layers 18/124/230/333/430. The precise arrangement of nanotubes 528 and/or sensing layer 530 may vary. For example, sensing layer 530 may be continuous, may pass over the top of the nanotubes 528 as shown, may coat or even "fill in" the interior of nanotubes 528, be intermittent or broken, or otherwise include one or more localized amino functional groups disposed along nanotubes 528.

Manufacturing any of the sensors disclosed herein may include a variety of different processes. For example, manufacturing any of the carbon dioxide sensors disclosed herein may include providing a sensing layer (such as any of those disclosed herein) and providing a reference layer. In many instances, the reference layer may be the same or substantially the same as the sensing layer (e.g., take the form of any of the sensing layers disclosed herein). In one example, the sensing layer and the reference layer may both include an amino group. When fabricating the sensor, the reference layer may be poisoned so that the reference layer will be substantially non-sensitive to the chemical of interest (e.g. carbon dioxide). Poisoning the reference layer may include, for example, applying an acid to the reference layer. In general, the use of an acid may be desirable because it may react with and neutralize amino groups on the reference layer. Any suitable acid may be utilized. For example, hydrochloric acid (HCL) may be used to poison the reference layer. It is contemplated that the acid may be applied to the reference layer using a direct printing process, if desired.

The manufacturing process may include preparing and/or manufacturing the sensing layer. As indicated above, some example sensing layers may include composites. Thus, manufacturing the sensing layer may include providing the components of the composite (e.g., the ionic liquid, the polymer or polymer layer, and/or the nanowires/nanotubes) in a suitable common solvent. The dissolved material, which in some cases may be gelatinous in nature, may then be cast. This may include casting one or more layers in any suitable arrangement. The resultant cast films may then be dried to remove the solvent and form the sensing layer.

In other embodiments, manufacturing the sensing layer may include deposition of one or more materials (e.g., dissolved in a suitable solvent) onto another material. For example, a polymer layer may provided. The polymer layer may be porous or otherwise made to include pores or cavities. A solution of sensing ionic liquid may be deposited in the pores or cavities of the polymer layer to form a composite layer or film. The resultant films may be dried to remove the solvent and form the sensing layer. The sensing ionic liquid may, in general, include an amino group. For example, the sensing ionic liquid may include an amino functionalized ionic liquid, 1-(4-amino butyl)-3 methylimidazolium hexafluorophosphate, 1-(2-amino ethyl)-3 methylimidazolium tetrafluoroborate, combinations thereof, or the like.

Another example method of manufacturing a carbon dioxide sensor may include providing a sensing layer, wherein the sensing layer includes an amino group and is configured to sense carbon dioxide. In some cases, the sensing layer may include a sensing ionic liquid, a polymer layer, one or more nanowires, one or more nanotubes, an amino functionalized ionic liquid and an amino functionalized carbon nanotube composite, an amino functionalized ion liquid and an amino group based polymer or polymer layer composite, or an amino functionalized carbon nanotube and an amino group based polymer or polymer layer composite. The method may further include providing a reference layer, wherein the reference layer includes an amino group. At least part of the reference layer may be poisoned so that it will be substantially non-sensitive to carbon dioxide. In some cases, poisoning the reference layer may include applying an acid to the reference layer. In some cases, the acid may be applied to the reference layer using a direct printing process.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A carbon dioxide sensor, comprising:
   a substrate;
   a sensing beam supported by the substrate, the sensing beam configured to resonate;
   a sensing layer disposed on the sensing beam, wherein the sensing layer includes an amino group and is configured to sense carbon dioxide;
   a reference beam supported by the substrate, the reference beam configured to resonate; and
   a reference layer disposed on the reference beam, wherein the reference layer includes an amino group that has been poisoned via reaction with an acid so that the amino group will be substantially non-sensitive to carbon dioxide.

2. The carbon dioxide sensor of claim 1, wherein the sensing layer includes a sensing ionic liquid.

3. The carbon dioxide sensor of claim 2, wherein the sensing ionic liquid includes an amino functionalized ionic liquid, 1-(4-amino butyl)-3 methylimidazolium hexafluorophosphate, 1-(2-amino ethyl)-3 methylimidazolium tetrafluoroborate, or combinations thereof.

4. The carbon dioxide sensor of claim 1, wherein the sensing layer includes a polymer layer.

5. The carbon dioxide sensor of claim 4, wherein the polymer layer includes an amino group based polymer, N-substituted polyallylamine, polydiallylamine, polytriallylamine, polyvinlylamine, poly(y-aminoproplyethoxy/propylethoxysilones) (PAPP), poly(y-aminopropylethody octadecylethoxysiloxane) (PAPO), or combinations thereof.

6. The carbon dioxide sensor of claim 1, wherein the sensing layer includes one or more nanowires or one or more nanotubes.

7. The carbon dioxide sensor of claim 6, wherein the one or more nanotubes include amino functionalized carbon nanotubes, carbon nanotubes with aliphatic amino groups situated at the end of an alkyl chain, or combinations thereof.

8. The carbon dioxide sensor of claim 1, wherein the sensing layer is a composite layer including an amino functionalized ionic liquid and an amino functionalized carbon nanotube composite.

9. The carbon dioxide sensor of claim 1, wherein the sensing layer is a composite layer including an amino functionalized ionic liquid and an amino group based polymer or polymer layer composite.

10. The carbon dioxide sensor of claim 1, wherein the sensing layer is a composite layer including an amino functionalized carbon nanotube and an amino group based polymer or polymer layer composite.

* * * * *